United States Patent [19]

Koch et al.

[11] 4,148,762
[45] Apr. 10, 1979

[54] COSMETIC CLEANING AGENTS CONTAINING BETAINES AND PROCESS

[75] Inventors: Karlheinz Koch, Haan; Fanny Scheuermann, Dusseldorf, both of Fed. Rep. of Germany

[73] Assignee: Henkel Kommanditgesellschaft auf Aktien, Dusseldorf, Fed. Rep. of Germany

[21] Appl. No.: 784,738

[22] Filed: Apr. 5, 1977

[30] Foreign Application Priority Data

Apr. 15, 1976 [DE] Fed. Rep. of Germany ....... 2616800

[51] Int. Cl.$^2$ .......................... C11D 1/88; C11D 1/94
[52] U.S. Cl. .................... 252/544; 252/546; 252/548; 252/DIG. 5; 252/DIG. 7; 252/DIG. 13; 260/501.13; 424/70
[58] Field of Search ......... 252/544, 546, 548, DIG. 5, 252/DIG. 7, DIG. 13, 527, 528; 260/501.13; 424/70

[56] References Cited

U.S. PATENT DOCUMENTS

| | | | |
|---|---|---|---|
| 3,700,607 | 10/1972 | Sundby et al. | 252/527 |
| 3,726,797 | 4/1973 | Sundby et al. | 252/527 X |
| 3,822,312 | 7/1974 | Sato et al. | 252/DIG. 13 |
| 3,888,797 | 6/1975 | Marumo | 252/DIG. 13 |
| 4,076,743 | 2/1978 | Koch et al. | 252/528 X |

*Primary Examiner*—Thomas J. Herbert, Jr.
*Attorney, Agent, or Firm*—Hammond & Littell

[57] ABSTRACT

The present invention relates to cosmetic cleaning agents containing surface-active betaines of the formula.

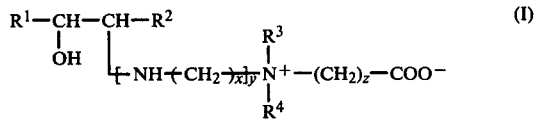

wherein $R^1$ and $R^2$ are aliphatic hydrocarbon radicals having 1 to 18 carbon atoms and/or hydrogen and the sum of the carbon atoms in $R^1$ and $R^2$ is 9 to 18; $R^3$ and $R^4$ are the same or different and are lower alkyl or alkylol groups having 1 to 4 carbon atoms, x is an integer of 2 to 4, y is either 0 or 1, and z is an integer of 1 to 4; as well as their application as cleaning agents, for example, in hair washing and bathing preparations.

17 Claims, No Drawings

COSMETIC CLEANING AGENTS CONTAINING BETAINES AND PROCESS

THE PRIOR ART

It is already known to incorporate ampholytes in cosmetic cleaning agents. Due to the fact that they have a germicidal effect on hair and skin fungi as well as on bacteria, and that they have an antistatic effect on the hair, these ampholytes are particularly valuable in hair-washing agents. However, a frequent disadvantage is that, owing to good substantivity relative to the hair, the hair becomes too greatly loaded with ampholytes, thus rapidly causing the hair to become greasy or stringy.

Therefore, the task arose of providing cosmetic cleaning agents, particularly hair-washing agents and bathing preparations based on ampholytes, which have all the advantages of the cleaning agents hitherto used, such as reducing the electrostatic charge on the hair, improving the fullness and the gloss of the dry hair, improving the wet combability, having satisfactory skin compatibility and leaving a pleasant skin feel after use, without at the same time leading to too great a residual concentration of cleaning agent on the hair.

OBJECTS OF THE INVENTION

It is an object of the present invention to provide a cosmetic cleaning agent composition having a content of surface-active betaines, which is particularly useful as a hair-washing and bathing agent, and reduces the electrostatic charge on the hair, improves the fullness and gloss of dry hair and its wet combability, and has satisfactory skin compatibility and a pleasant skin feel, without leaving an excessive residue on the hair.

It is another object of the present invention to provide a cosmetic cleaning agent composition containing betaines of the formula

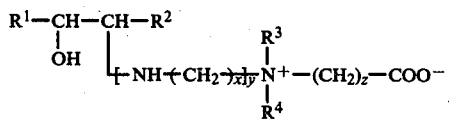

wherein $R^1$ and $R^2$ are aliphatic hydrocarbon radicals having 1 to 18 carbon atoms and/or hydrogen and the sum of the carbon atoms in $R^1$ and $R^2$ is 9 to 18; $R^3$ and $R^4$ are the same or different and are alkyl or alkylol groups having 1 to 4 carbon atoms, x is an integer of 2 to 4, y is either 0 or 1, and z is an integer of 1 to 4, and a carrier therefor.

It is a further object of the present invention to develop a process for cleaning the hair and skin of warm-blooded animals comprising topically applying to the hair and skin a safe but effective amount of the above composition.

These and other objects of the present invention will become more apparent as the description thereof proceeds.

DESCRIPTION OF THE INVENTION

The above objects have been achieved by the discovery of a cosmetic cleaning agent comprising a surface-active betaine of the general formula

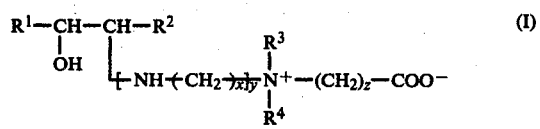

in which $R^1$ and $R^2$ are the same or different and are aliphatic hydrocarbon, preferably alkyl, radicals of 1 to 18 carbons atoms or hydrogen, provided that the sum of the number of carbon atoms of $R^1$ and $R^2$ is 9 to 18; $R^3$ and $R^4$ are the same or different and are lower alkyl or alkylol groups of 1 to 4 carbon atoms; x is an integer of from 2 to 4; y is either 0 or 1; and z is an integer of from 1 to 4; and a carrier therefor.

An interesting group of betaines of the instant invention are those wherein y is o. While these compounds differ from the others within formula I in having the quaternary ammonium nitrogen directly attached to the

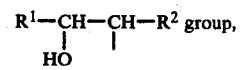 group, they are similarly effective in overcoming the disadvantages associated with prior art ampholytes used in cosmetic cleaning agent.

Betaines within formula (I) above are disclosed in U.S. application Ser. No. 758,035, filed January 10, 1977, now U.S. Pat. No. 4,076,743, Feb. 28, 1978, together with a process for making them. The betaines of formula (I) above wherein $R^1$ or $R^2$ is hydrogen are, however, not disclosed in this application.

The betaines used in the cosmetic cleaning agents of the invention can be manufactured by reacting an aminoalkanol of the formula II

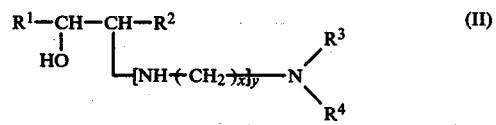

wherein the radicals $R^1$ to $R^4$, and x and y, are as defined in Formula I above, with an equimolar quantity of a monohalocarboxylic acid, or a salt thereof, dissolved in water. A reaction of this type is shown in Houben-Weyl, Methoden der organischen Chemie, Volume 11/2 (1958), page 630.

When two amino groups are present in the starting aminoalkanol (i.e., when y equals 1), a product, in which the halocarboxylic, preferably chlorocarboxylic acid has reacted with the secondary nitrogen atom of the aminoalkanol and not the tertiary nitrogen atom of the compound, can be formed in an alternative reaction during quaternization. This alternative or secondary product has the formula

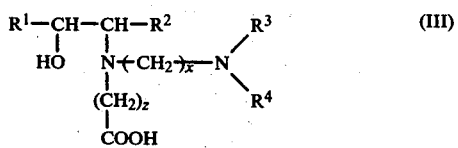

wherein $R^1$-$R^4$ and x and z have the above-stated meanings, and can amount to up to 20 percent by weight of the total quantity of the betaines of formula I above which are formed during the reaction.

In the latter instance, the invention provides a mixture consisting essentially of (A) a compound of the formula

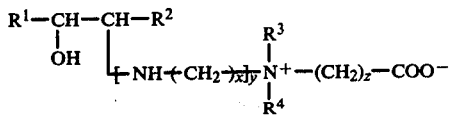

(I)

and (B) a minor amount of a compound of the formula:

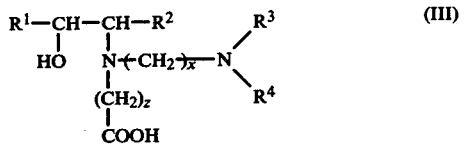

(III)

(or salt thereof), wherein $R^1$–$R^4$, x, y and z have the above-stated meanings and wherein the weight of component (B) is no more than about 20 percent of the weight of component (A). The weight of component (B) can vary from a very small weight % to about 20 weight % of component A, as e.g. from about 1% to 20% thereof.

It was unexpectedly found that the presence of this minor amount of compound III is in no way disadvantageous. Thus, the above-described mixture can be used in the same manner as the compounds of formula I in pure state.

The invention naturally includes both the betaines of formula I in pure state, the mixtures as described in the two immediately preceding paragraphs and any mixture of said betaines of formula I in pure state and said mixtures described in the two immediately preceding paragraphs.

The starting aminoalkanols (formula II above) can be produced analogously to the processes disclosed in German patent application DOS 25 20 267.9, and U.S. copending Pat. application Ser. No. 683,322, filed May 5, 1976, the teachings of which U.S. patent application are incorporated herein by reference, by reacting one or more epoxyalkanes of the formula:

(IV)

with one or more amines of the formula

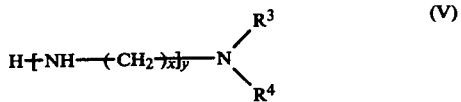

(V)

wherein $R^1$–$R^4$, x and y have the meanings shown above.

Epoxyalkanes of the Formula IV above having non-terminal or terminal epoxy groups, 11 to 20 carbon atoms and preferably an unbranched alkyl chain, are suitable as starting materials. Mixtures of epoxyalkanes are also useful, such as those having different chain lengths and/or the epoxy group in isomeric positions. The epoxyalkanes of Formula IV are obtainable in a known manner by epoxidation of corresponding olefins or olefin mixtures. The above-mentioned mixtures of epoxyalkanes have been found to be especially suitable in the production of the betaines of the present invention. Such mixtures of epoxyalkanes having at least 11 carbon atoms in their chain lengths give satisfactory results.

Suitable amines of the Formula V are secondary amines such as dimethylamine, methylethylamine, diethylamine, dibutylamine and diethanolamine, as well as asymmetrically disubstituted diamines such as N,N-dimethylethylenediamine, N,N-dimethylpropylenediamine, N-methyl-N-ethylethylenediamine, N,N-diethylethylenediamine, N-N-diethanolpropylenediamine and N,N-diethanoltetramethylenediamine. The radicals $R^3$ and $R^4$ of the amines are preferably methyl radicals.

Monohalocarboxylic acids having 1 to 5 carbon atoms or salts thereof, preferably sodium chloroacetate, can be used in the quarternization reaction of the aminoalkanols.

In an advantageous modification of the betaines of the invention, neutralization of the betaines of Formula I or of their mixture with compounds of Formula III is effected by acid treatment, as e.g. by treatment with inorganic acids or organic carboxylic acids, such as hydrochloric, sulfuric, phosphoric, acetic, chloracetic, trichloroacetic, propionic, etc., in accordance with techniques well-known in the art. The neutralization advantageously provides a pH of about 5–7, preferably about 6. Such neutralized betaines serve as extremely useful cosmetic cleaning agent additives of the instant invention and have the same advantageous properties as the betaines of Formula I.

Among the many betaines included within the definition of Formula I may be mentioned two somewhat different classes of compounds. One of these is derived from starting epoxyalkanes consisting of mixtures of epoxides of various chain lengths, in which mixtures the epoxide groups are substantially all located at non-terminal positions. These compounds have excellent properties, as e.g. in shampoos and bathing preparations.

Another type of betaines within the definition of Formula I which may be mentioned are those derived from starting epoxyalkanes consisting of mixtures of epoxides of various chain lengths, in which mixtures there is a high weight percent of epoxides having terminal epoxide groups, as e.g. over 50 weight percent. While such mixtures differ structurally from those mixtures having principally non-terminal epoxide groups, they nevertheless yield betaines from which very useful cosmetic cleaning agents can be derived.

Even though, in principle, it is possible to produce the cosmetic cleaning agents of the invention with the sole use of the betaines described above as surface-active substances, the betaines of the invention are generally used, in practice, in combination with other surfactants, preferably anionic surfactants, such as alkylsulfates, alkylethersulfates, alkyarylethersulfates, etc. Even when large quantities of betaines are used, it is possible to manufacture clear, turbid or emulsion-like preparations having satisfactory stability, whose foaming power is scarcely reduced despite the high concentration of betaines.

The cosmetic cleaning agents of the invention can contain the betaines in quantities of from 1 to 50 percent by weight, relative to the total cosmetic cleaning agent, although, in practice, the value of 30 percent by weight is not exceeded. The quantity preferably used is from 3 to 10 percent by weight, relative to the total cosmetic cleaning agent.

The cosmetic cleaning agents of the invention can also contain, in addition to the betaines, conventional quantities of all the customary constituents used in such products, such as quantities of from 5 to 30 percent by weight of ionic surfactants of the alkylsulfate, alkylethersulfate and alkylarylethersulfate type, quantities of from 0.5 to 5 percent by weight of fatty acid alkanolamides, quantites of 0 to 10 percent by weight of skin re-greasing agents, relative to the total weight of the preparation, and water. The appropriate quantity of water for the cosmetic cleaning agent can be readily determined by one skilled in the art. An amount of water in the range from about 5–70 weight percent relative to the total weight of the preparation, serves as an example of the quantity of water which might generally be present in the cosmetic cleaning agents. Further additional agents which can be used in small quantities are, for example, perfumes, preservatives, albumen hydrolysates, anti-dandruff effective substances, and inorganic salts for the purpose of regulating the viscosity.

The essential advantage obtainable by the betaines of the invention resides in the fact that, along with an excellent reduction in the electrostatic charging of the hair and an improvement in its fullness, gloss, and wet-combability, the betaines do not cause heavy loading of the hair. When used in bathing preparations, the betaines of the invention are distinguished from other ampholytes in that the pleasant skin feel after bathing can be obtained with the use of substantially smaller quantities.

Furthermore, the products of the invention have a very satisfactory skin compatibility as well as an only slight neutral odor. This odor is not noticeable in cosmetic formulations, even without the addition of a perfume ingredient to said formulations.

The invention also includes a process for cleaning the hair and skin of warm-blooded animals comprising topically applying to said hair and skin a safe but effective amount of the cosmetic cleaning agent of the invention, as hereinbefore defined.

The following examples are intended to illustrate the subject of the invention without, however, limiting it to these examples.

EXAMPLES

EXAMPLE 1

PREPARATION OF BETAINES

The production of some of the betaines of the invention is described below.

PRODUCT A 255 gm (approximately 1 mole) of a $C_{15-18}$ epoxide mixture (with the following chain length distribution of non-terminal epoxides: approximately 26 percent by weight of $C_{15}$, approximately 35 percent by weight of $C_{16}$, approximately 31 percent by weight of $C_{17}$, and approximately 6 percent by weight of $C_{18}$), 612 gm (6 moles) of N,N-dimethyl-1,3-propylenediamine and 9 gm (0.5 mole) of water were stirred for 5 hours in an autoclave at 200° C. The maximum pressure was 25 to 30 atmospheres. The surplus diamine was distilled off after the reaction, and the 305 gm (85% of theory) of the aminoalkanol obtained were added to an aqueous solution of an equimolar quantity (99 gm) of the sodium salt of chloroacetic acid. This mixture was stirred at 80 to 100° C. until an homogeneous phase was formed in a half hour, and if required, can be neutralized with acetic acid. The physical data of the betaine obtained are summarized in Table 1.

PRODUCT B 112 gm (1.1 moles) of N,N-dimethyl-1,3-propylenediamine were added dropwise to 198 gm (approximately 1 mole) of a $C_{11-14}$ epoxide mixture (with the following chain length distribution of non-terminal epoxides: approximately 22 percent by weight of $C_{11}$, approximately 30 percent by weight of $C_{12}$, approximately 26 percent by weight of $C_{13}$ and approximately 22 percent by weight of $C_{14}$), 18 gm (0.2 mole) of glycerine and a few drops of N,N-dimethyl-1,3-propylenediamine. The mixture was subsequently stirred for a further 2 hours under reflux (200° to 210° C.), and the glycerine was washed out with water. 258 gm (90% of theory) of the aminoalkanol obtained were purified by distillation and added to an aqueous solution of 104 gm of the sodium salt of chloroacetic acid and the mixture was stirred at 80 to 90° C. for a half hour until a homogeneous phase had formed. The betaine has the physical data given in the following Table 1.

Further betaines of the invention were produced analogously to the above processes by which products A and B were obtained. The physical data of products A and B and of these additional betaines are presented in the following Table 1.

Table 1

| Product | Epoxide $R^2$ | Amine $R^3$ | $R^4$ | x | y | Active content (%) | NaCl content (%) | pH value (1% solution) |
|---|---|---|---|---|---|---|---|---|
| A | $C_{15} - C_{18}$ | $CH_3$ | $CH_3$ | 3 | 1 | 35.6 | 4.35 | 8.40 |
| B | $C_{11} - C_{14}$ | $CH_3$ | $CH_3$ | 3 | 1 | 35.7 | 5.54 | 9.05 |
| A neutr.[6] | $C_{15} - C_{18}$ | $CH_3$ | $CH_3$ | 3 | 1 | 40.8 | 4.53 | 7.00 |
| B neutr.[6] | $C_{11} - C_{14}$ | $CH_3$ | $CH_3$ | 3 | 1 | 38.6 | 5.4 | 7.00 |
| C | $C_{11} - C_{14}$[1] | $CH_3$ | $CH_3$ | — | 0 | 47.9 | 8.75 | 6.05 |
| D | $C_{15} - C_{18}$[2] | $CH_3$ | $CH_3$ | — | 0 | 30.6 | 4.30 | 6.05 |
| E | $C_{12}/C_{14}$[3] H[9] | $CH_3$ | $CH_3$ | — | 0 | 30.1 | 4.79 | 6.05 |
| F | $C_{14}/C_{16}$[4] H[9] | $CH_3$ | $CH_3$ | — | 0 | 28.5 | 4.10 | 6.05 |
| G | $C_{16}/C_{18}$[5] H[9] | $CH_3$ | $CH_3$ | — | 0 | 18.5 | 1.61 | 6.05 |
| H | $C_{12}/C_{14}$[7] H[9] | $C_2H_5$ | $C_2H_5$ | — | 0 | 33.8 | 4.51 | 6.05 |

Table 1-continued

| Product | Epoxide | | Amine | | | | Active content (%) | NaCl content (%) | pH value (1% solution) |
|---|---|---|---|---|---|---|---|---|---|
| | | $R^2$ | $R^3$ | $R^4$ | x | y | | | |
| I | $C_{14}/C_{16}{}^{8)}$ | $H^{9)}$ | $CH_3$ | $CH_3$ | 3 | 1 | 36.2 | 4.7 | — |

[1] Epoxide mixture as described in production Example B
[2] Epoxide mixture as described in production Example A
[3] Epoxide mixture of the chain length distribution of approximately
  60 percent by weight of $C_{12}$, approximately
  39 percent by weight of $C_{14}$ and approximately
  87 percent by weight of epoxides having a terminal epoxy group
[4] Epoxide mixture of the chain length distribution of approximately
  60 percent by weight of $C_{14}$, approximately
  39 percent by weight of $C_{16}$, and approximately
  82 percent by weight of epoxides having a terminal epoxy group
[5] Epoxide mixture of the chain length distribution of approximately
  46 by weight of $C_{16}$, approximately
  45 percent by weight of $C_{18}$, and approximately
  60 percent by weight of epoxides having a terminal epoxy group
[6] Product neutralized with acetic acid.
[7] Same epoxide mixture as in product E above.
[8] Same epoxide mixture as in product F above.
[9] $R^2$ is hydrogen to the approximate extent indicated in (3)–(5) and (7)–(8) above.

EXAMPLE 2

PHYSIOLOGICAL COMPATIBILITY OF BETAINES

The satisfactory physiological compatibility of the products of the invention, particularly their satisfactory skin compatibility, is shown by the results given hereinafter for product B neutralized with acetic acid.

The acute toxicity was determined by oral doses administered to mice. An $LD_{50}$ value of 3.75 g/kg was employed.

A. Testing the skin compatibility on hairless mice

The produce was applied in a 50% by weight concentration (aqueous solution) and was left on the skin for 1 hour and then the skin was washed. There were no findings of skin irritation after this period of contact. In another series of tests, a 5% by weight aqueous solution of the product was applied once daily to the same place for 5 days. There were no findings of skin irritation after 5 days.

B. Mucous membrane compatibility test on rabbits' eyes

The product was dripped in a 1% by weight aqueous solution into the rabbit's eye. After a period of contact of 15 seconds, the conjunctiva exhibited a slight degree of redness and slight swelling which, however, soon disappeared, with the result that the condition of the eye was normal after 24 hours.

Some Examples of the cosmetic cleaning agents of the invention are given hereinafter.

EXAMPLE 3

| Foam bath concentrate | Parts by weight |
|---|---|
| Sodium lauryl ether sulfate with 27 to 28% of active washing substance | 40 |
| Product B, neutralized | 30 |
| Water-soluble perfume | 4 |
| Water | 26 |

EXAMPLE 4

| Foam bath concentrate | Parts by weight |
|---|---|
| Sodium lauryl ether sulfate with 27 to 28% of active washing substance | 70 |
| Product B, neutralized | 15 |
| Cetyl-stearyl alcohol adduct with approximately 12 moles of ethylene oxide | 2 |
| Perfume | 2 |
| Water | 11 |

The other products A and C to I, optionally after a corresponding neutralization with acetic acid, can be used with equally good results instead of neutralized product B.

EXAMPLE 5

| Cream foam bath | Parts by weight |
|---|---|
| Sodium lauryl ether sulfate with 27 to 28% active washing substance | 70 |
| 2-octyl-dodecanol | 5 |
| Product B, neutralized | 5 |
| Mixture of fatty alcohol ether sulfates with brightening substances which impart luster (Euperlan PK 771 ®) | 10 |
| Sodium chloride | 1.5 |
| Perfume oil | 1 |
| Water | 7.5 |

EXAMPLE 6

| Foam bath, clear | Parts by weight |
|---|---|
| Triethanolamine lauryl sulfate with 47 to 48% of active washing substance | 30 |
| Coconut fatty acid diethanolamide | 1 |
| Product B, neutralized | 5 |
| Sodium chloride | 5 |
| Water-soluble perfume | 2 |
| Water | 57 |

EXAMPLE 7

| Foam bath emulsion with luster | Parts by weight |
|---|---|
| Sodium lauryl ether sulfate with 35 to 37% of active |  |

-continued

| Foam bath emulsion with luster | Parts by weight |
|---|---|
| Washing substance | 40 |
| Sodium lauryl ether sulfate with 27 to 28% of active washing substance | 15 |
| Coconut fatty acid diethanolamide | 2 |
| Product B, neutralized | 5 |
| Perfume oil | 1 |
| Water | 37 |

EXAMPLE 8

| Baby foam bath | Parts by weight |
|---|---|
| Sodium lauryl ether sulfate with 27 to 28% of active washing substance | 18 |
| Polyoxyethyleneglycerolmonostearate | 5 |
| Product B, neutralized | 5 |
| Vegetable extract Extrapon 4/special ® | 5 |
| Azulene | 0.1 |
| Water | 66.9 |

All the aforementioned bathing preparations produce a pleasant skin feel after bathing. The skin feels smooth, supple and soft without feeling greasy. This pleasant skin feeling is not confined to a short period of time after bathing, but lasts for a long part of the day. Only small quantities of approximately 5 percent by weight relative to the total preparation are needed to impart these satisfactory conditioning properties to the bathing preparation, while with the ampholytes hitherto used, comparable conditioning effects could be obtained only with considerably larger quantities of 10 to 15 percent by weight relative to the total preparation.

The other products A and C to I, optionally after a corresponding neutralization with acetic acid, can be used with equally good results in the foam baths of Examples 5 to 8 instead of neutralized product B.

EXAMPLE 9

| Shampoo | Parts by Weight |
|---|---|
| Sodium lauryl ether sulfate with 27 to 28% active washing substance | 30 |
| Sodium chloride | 2 |
| Coconut fatty acid diethanolamide | 2 |
| Product B, neutralized | 5 |
| Anti-dandruff effective substance | 1 |
| Protein hydrolysate | 1 |
| Scent component | 1 |
| Water | 58 |

EXAMPLE 10

| Shampoo | Parts by weight |
|---|---|
| Sodium lauryl ether sulfate with 35 to 37% active washing substance | 30 |
| Sodium chloride | 1 |
| Product B, neutralized | 5 |
| Scent component | 1 |
| Water | 63 |

EXAMPLE 11

| Shampoo for greasy hair | Parts by weight |
|---|---|
| Magnesium lauryl ether sulfate with 29 to 31% active washing substance | 30 |
| Coconut fatty acid diethanolamide | 5 |
| Product B, neutralized | 5 |
| Tactocut powder M 71 ® (the Stockhausen firm) | 3 |
| Protein hydrolysate | 1 |
| Preservative | 0.2 |
| Scent component | 1 |
| Water | 54.8 |

The other products A and C to I, optionally after a neutralization with acetic acid, can also be used with equally good results in the above-mentioned shampoo formulations 9 to 11 instead of neutralized product B.

We claim:

1. A cosmetic cleaning agent, comprising an acid neutralized derivative of a surface-active betaine of the formula

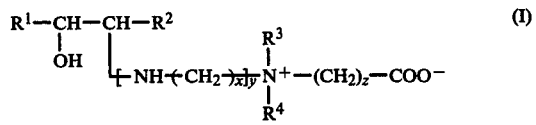

wherein
R$^1$ and R$^2$ are the same or different and are alkyl radicals of 1 to 18 carbon atoms, provided that the sum of the number of carbon atoms of R$^1$ and R$^2$ is 9 to 18;
R$^3$ and R$^4$ are the same or different and are lower alkyl or alkylol groups of 1 to 4 carbon atoms; x is an integer of from 2 to 4; y is 1; and z is an integer of from 1 to 4; and an anionic surfactant in a quantity of from 5 to 30 percent by weight, relative to the total weight of the agent; and a carrier therefor.

2. The agent of claim 1 wherein z is 20.

3. The agent of claim 1 wherein both R$^3$ and R$^4$ are methyl or one of R$^3$ and R$^4$ is methyl.

4. The agent of claim 3 wherein both R$^3$ and R$^4$ are methyl.

5. The agent of claim 1 which contains the surface-active member in a quantity of from 1 to 50 percent by weight, relative to the total weight of the agent.

6. The agent of claim 1 which contains the surface-active member in a quantity of from 3 to 10 percent by weight, relative to the total weight of the agent.

7. The agent of claim 1 where R$^1$ and R$^2$ are unbranched alkyl groups.

8. The agent of claim 1 wherein R$^3$ and R$^4$ are methyl, x is 3, y is 1 and z is 1.

9. A process for cleaning the hair and skin of warm-blooded animals comprising topically applying to said hair and skin a safe but effective amount of a cosmetic cleaning agent, comprising an acid neutralized derivative of a surface-active betaine of the formula

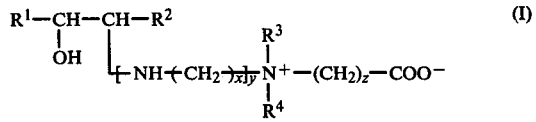

wherein $R^1$ and $R^2$ are the same or different and are alkyl radicals of 1 to 18 carbon atoms, provided that the sum of the number of carbon atoms of $R^1$ and $R^2$ is 9 to 18; $R^3$ and $R^4$ are the same or different and are lower alkyl or alkylol groups of 1 to 4 carbon atoms; x is an integer of from 2 to 4; y is 1; and z is an integer of from 1 to 4; and a carrier therefor.

10. The process of claim 9 wherein z is 1.

11. The process of claim 9 wherein both $R^3$ and $R^4$ are methyl or one of $R^3$ and $R^4$ is methyl.

12. The process of claim 11 wherein both $R^3$ and $R^4$ are methyl.

13. The process of claim 9 wherein the acid neutralized derivative of the surface-active betaine is present in a quantity of from 1 to 50 percent by weight, relative to the total weight of the agent.

14. The process of claim 9 wherein the acid neutralized derivative of the surface-active betaine is present in a quantity of from 3 to 10 percent by weight, relative to the total weight of the agent.

15. The process of claim 9, wherein, in addition to the acid neutralized derivative of the surface-active betaine, an anionic surfactant is present in a quantity of from 5 to 30 percent by weight, relative to the total weight of the agent.

16. The process of claim 9 wherein $R^1$ and $R^2$ are unbranched alkyl groups.

17. The process of claim 9 wherein $R^3$ and $R^4$ are methyl, x is 3, y is 1 and z is 1.

* * * * *

UNITED STATES PATENT AND TRADEMARK OFFICE
CERTIFICATE OF CORRECTION

PATENT NO. : 4,148,762
DATED : April 10, 1979
INVENTOR(S) : KARLHEINZ KOCH et al.

It is certified that error appears in the above-identified patent and that said Letters Patent are hereby corrected as shown below:

Column 2, line 9, "carbons" should read -- carbon --.
Column 4, line 22, "choracetic" should read -- chloroacetic --.
Column 10, line 42, "z is 20" should read -- z is 1 --.

Signed and Sealed this

Eleventh Day of March 1980

[SEAL]

Attest:

SIDNEY A. DIAMOND

Attesting Officer

Commissioner of Patents and Trademarks